US 8,648,727 B2

(12) United States Patent
Caldwell et al.

(10) Patent No.: US 8,648,727 B2
(45) Date of Patent: Feb. 11, 2014

(54) WIRELESS CODE GAME ENURESIS ALARM FOR THE TREATMENT OF ENURESIS

(75) Inventors: Patrina Ha Yuen Caldwell, Westmead (AU); Michael Lance Dickinson, Westmead (AU); James Charles Kerr McCauley, Westmead (AU); Geoffrey Gordon Wickham, Westmead (AU)

(73) Assignees: The Sydney Children's Hospitals Network (Randwick and Westmead), Westmead (AU); The University of Sydney, Sydney (AU)

( * ) Notice: Subject to any disclaimer, the term of this patent is extended or adjusted under 35 U.S.C. 154(b) by 236 days.

(21) Appl. No.: 13/062,487

(22) PCT Filed: Sep. 22, 2009

(86) PCT No.: PCT/AU2009/001257
§ 371 (c)(1),
(2), (4) Date: Apr. 8, 2011

(87) PCT Pub. No.: WO2010/034054
PCT Pub. Date: Apr. 1, 2010

(65) Prior Publication Data
US 2011/0199218 A1       Aug. 18, 2011

(30) Foreign Application Priority Data
Sep. 23, 2008   (AU) .................................. 2008904962

(51) Int. Cl.
*G08B 23/00*            (2006.01)
(52) U.S. Cl.
USPC ................... 340/575; 340/573.2; 340/539.12; 340/603; 340/573.1; 600/300

(58) Field of Classification Search
USPC .................. 340/573.1, 573.5, 539.11, 539.12, 340/603–625, 604–5; 600/300; 304/573.1, 304/573.5, 539.11, 539.12, 603–625, 604–5
See application file for complete search history.

(56) References Cited

U.S. PATENT DOCUMENTS 4,163,449 A * 8/1979 Regal ............................ 128/886
5,043,704 A * 8/1991 Blakeney .................... 340/573.5
(Continued)

FOREIGN PATENT DOCUMENTS

WO          2007100958         9/2007
WO     WO 2007100958 A1 *    9/2007  ............... A61B 5/00

OTHER PUBLICATIONS

Bower, et al. (1996) "The Epidemiology of Childhood Enuresis in Australia" Br. J. Urol. 78(4):602-606.

(Continued)

*Primary Examiner* — Benjamin C Lee
*Assistant Examiner* — Chico A Foxx
(74) *Attorney, Agent, or Firm* — Carol L. Francis; Bozicevic, Field & Francis LLP

(57) ABSTRACT

A system (10) and method for use by a subject with a sleep disorder, such as nocturnal enuresis. The system (10) comprises at least one sensor (11) that detects at least one attribute of the sleep disorder, for example urine, and outputs at least a first signal on or after detection of that attribute. The system (10) further comprises a control device (12) that comprises an arousal device (14), such as a loudspeaker, that activates on or after receipt of the first signal, an interactive device (15) that is actuable by the subject to deactivate or modify the operation of the arousal device (14) and an output device (16) for delivering an output to the subject. The output being delivered on or after deactivation or modification of the arousal device (14).

17 Claims, 2 Drawing Sheets

(56) References Cited

U.S. PATENT DOCUMENTS

| | | | | |
|---|---|---|---|---|
| 5,074,317 | A * | 12/1991 | Bondell et al. | 128/886 |
| 6,325,066 | B1 * | 12/2001 | Hughes et al. | 128/885 |
| 6,585,518 | B1 * | 7/2003 | Jenkins et al. | 434/236 |
| 2003/0199945 | A1 * | 10/2003 | Ciulla | 607/48 |
| 2004/0097871 | A1 * | 5/2004 | Yerushalmy | 604/65 |
| 2005/0033250 | A1 * | 2/2005 | Collette et al. | 604/361 |
| 2005/0190065 | A1 * | 9/2005 | Ronnholm | 340/575 |
| 2010/0228315 | A1 * | 9/2010 | Nielsen | 607/42 |

OTHER PUBLICATIONS

Caldwell, et al. (2005) "4. Bedwetting and Toileting Problems in Children" Med. J. Aust. 182(4):190-195.

Glazener & Evans, et al. (2002) "Desmopressin for Nocturnal Enuresis in Children (Review)" Cochrane Database Syst. Rev. (3):CD002112.

Glazener, et al. (2006) "Alarm Interventions for Nocturnal Enuresis in Children (Review)" Evid.-Based Child Health 1 (1):9-97.

Hägglöf, et al. (1997) "Self-Esteem before and after Treatment in Children with Nocturnal Enuresis and Urinary Incontinence" Scand. J. Urol. Nephrol. Suppl. 183:79-82.

Hägglöf, et al. (1998) "Self-Esteem in Children with Nocturnal Enuresis and Urinary Incontinence: Improvement of Self-Esteem after Treatment" Eur. Urol. 33(Suppl. 3):16-19.

International Children'S Continence Society "New Research Highlights That Bedwetting Children Suffer from Impaired Brain Function, Sleep Arousal Disturbance and Bladder Dysfunction" PR Newswire Europe, Sha Tin, Hong Kong, Nov. 30, 2007.

Morison (1998) "Parents' and Young People's Attitudes towards Bedwetting and Their Influence on Behaviour, Including Readiness to Engage in and Persist with Treatment" Br. J. Urol. 81(Suppl. 3):56-66.

Theunis, et al. (2002) "Self-Image and Performance in Children with Nocturnal Enuresis" Eur. Urol. 41(6):660-667.

Watanabe & Azuma (1989) "A Proposal for a Classification System of Enuresis Based on Overnight Simultaneous Monitoring of Electroencephalography and Cystometry" Sleep 12(3):257-264.

Yeung, et al. (2002) "Reduction in Nocturnal Function Bladder Capacity Is a Common Factor in the Pathogenesis of Refractory Nocturnal Enuresis" BJU Int. 90(3):302-307.

Young & Morgan (1973) "Rapidity of Response to the Treatment of Enuresis" Dev. Med. Child. Neurol. 15 (4):488-496.

Zung, et al. (1961) "Response to Auditory Stimulation during Sleep. Discrimination and Arousal as Studied with Electroencephalography" Arch. Gen. Psychiatry 4:548-552.

* cited by examiner

WIRELESS CODE GAME ENURESIS ALARM FOR THE TREATMENT OF ENURESIS

CROSS-REFERENCE TO RELATED APPLICATIONS

The present application claims priority from Australian Provisional Patent Application No 2008904962 filed on 23 Sep. 2008, the content of which is incorporated herein by reference.

FIELD OF THE INVENTION

The present relates to a system for use in the treatment of sleep disorders such as enuresis.

BACKGROUND OF THE INVENTION

There are a number of known sleep disorders that have a significant impact on sufferers.

Bedwetting (enuresis), particularly nocturnal enuresis, is a common childhood sleep disorder. For example, in Australia it is believed to affect up to 750,000 children, with around 18% of school-aged children wetting at least once per week and around 2.4% wetting nightly. Bedwetting has a significant psychosocial impact on children who are often treated as social outcasts. Children miss out on important activities such as overnight school excursions and sleep-overs and in effect live in fear of exposure of their disorder. A study has suggested that bedwetting may have far-reaching consequences including effects on self-perception, interpersonal relationships, sexual activity and quality of life. Children with bedwetting also commonly have lower self esteem, however, it has been shown this will improve with successful treatment. Unfortunately, bedwetting is often trivialised, and in Australia, for example, only around 34% of families seek professional help, with many people not knowing where to go for help or being told that the child will eventually "grow out of it".

Treatment for bedwetting is available, with an enuresis alarm generally considered the most effective treatment. Studies suggest, however, that despite the availability of this treatment, many children (between around 25 to 35%) fail alarm training.

Clinical observations on children undergoing alarm training suggest that those who fail to wake on operation of the enuresis alarm are more likely to fail alarm therapy.

One type of enuresis alarm is the bell-and-pad bed alarm. Wired body worn alarm and wireless body worn alarms are also known. The bell-and-pad bed alarm relies on use of a relatively large urine mat sensor that is placed on the child's bed at night, with the child sleeping on top. In the case of body worn alarms, the sensor can be placed in the child's underpants. When the child wets during the night, the urine triggers the sensor, resulting in a relatively loud noise emitting from the alarm device. The noise wakes the child conditioning him/her to recognise the sensation of a full bladder and to hopefully inhibit urination or waken. The disadvantages of the bell-and-pad alarm include the loudness of the alarm (which usually wakes the entire household), the children complaining of not being able to wear underpants or pants to bed (as it delays the time for the urine to reach the sensor), increased washing (as the bed linen is still usually wet) and/or dislodgement of the sensor which results in treatment failure.

While wired and wireless body worn devices address some of these disadvantages, successful treatment of enuresis is still considered too low. For example, it has been observed by one of the current inventors that around 82% of children who presented to an incontinence clinic as having failed alarm training did not wake to the alarm sounding.

An example of another sleep disorder is bruxism. The teeth grinding associated with this sleep disorder can be a quite debilitating problem and can result in jaw pain, headache and teeth damage.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

SUMMARY OF THE INVENTION

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The present application is directed in part to a system suitable for the treatment of sufferers of certain kinds of sleep disorders and where it is desired to arouse the subject to a certain desired level.

The system is predicated at least in part on the notion that a subject's reluctance to wake up fully to the sound of an alarm during the night is understandable. For example, in the case of enuresis, even though some children acknowledge being aware of an alarm sounding during the night, most are reluctant to wake fully and get out of bed to void, which is necessary for alarm success.

According to a first aspect, the present application is directed to a system for use by a subject with a sleep disorder comprising:

at least one sensor that detects at least one attribute of the sleep disorder and outputs at least a first signal on or after detection of said attribute; and a control device comprising:
  an arousal device that activates on or after receipt of said first signal by said control device;
  an interactive device actuable by said subject to deactivate or modify the operation of said arousal device; and
  an output device for delivering an output to said subject, said output being delivered on or after deactivation or modification of the arousal device.

According to a second aspect, the present application is directed to a control device for use by a subject with a sleep disorder comprising:

an arousal device that activates on or after receipt by said control device of a first signal from at least one sensor that detects at least one attribute of the sleep disorder;

an interactive device actuable by said subject to deactivate or modify the operation of said arousal device; and an output device for delivering an output to said subject, said output being delivered on or after deactivation or modification of the arousal device.

In these aspects, the system and/or device can be used by a subject with a single sleep disorder. In another embodiment, the system and/or device can be capable of use by a subject with two or more sleep disorders. In this embodiment, the system and/or device can be used in the simultaneous treatment of two or more sleep disorders or be used for the treatment of just one sleep disorder at a time.

The one or more sleep disorders suffered by the subject can be selected from the group comprising enuresis including nocturnal enuresis, bruxism, sleepwalking, sleep talking, and/or night terrors.

The subject can be a child, including a child between the ages or about 3-18 years, more particularly between the ages of about 3-12 years, even more particularly between the ages of about 5-9 years. In another embodiment, the subject can be an adult.

During use of the system or device, and in particular before going to sleep, the subject is informed or reminded that if they are awoken by the arousal device, they should actuate the interactive device and note and remember the output of the output device. The subject can then be rewarded, for example in the morning, if they can appropriately recall the output of the output device. The provision of a reward for becoming sufficiently aware to firstly actuate the interactive device and secondly remember the output is anticipated by the current inventors to encourage a relatively higher degree of cognitive arousal in the subject than would be the case if the control device did not have both an interactive device and an output device that work in combination in the manner defined herein.

Once having reached that level of cognitive arousal, it also anticipated that the subject will act on the reason for activation of the sensor. For example, in the case of nocturnal enuresis the subject will be sufficiently aroused to realise that they need to void and will go to the toilet before returning to bed to sleep.

The output of the output device can change each time that the interactive device is appropriately actuated by the subject following operation of the arousal device. In another embodiment, the output can change from use to use or night to night for a period before recycling. As an example only, the output can change eight times before recycling. If the outputs are recycled, they can recycle in the same order or a different order to a previous cycle.

The output device can be a visual display device, an auditory device, and/or an audiovisual device. The output device can also comprise a device that is touchable by the subject and which has a distinctive feel that can be described by the subject. This latter embodiment may have application for children that are blind or have impaired eyesight and/or hearing.

In one embodiment, the visual device can comprise a display screen, for example a television screen, a projection screen, a liquid crystal display (LCD) or plasma screen. The screen can display a number, a word, a symbol, a picture, a photo, a colour, and/or a combination of any of these.

In the case of the auditory device, the device can comprise a loudspeaker that outputs an auditory output. The volume of the output can be pre-set. In another embodiment, the volume can be adjustable. Preferably, adjustment of the volume, if possible, requires entry of a code or the like to prevent the subject undesirably lowering the volume. In one embodiment, the volume of the auditory output can be about 90 dB if heard at a distance of 30 cm, in another, about 85 dB(A) if heard at a distance of about 1 m. Use of relatively louder or softer volumes can be envisaged.

In one embodiment, the same device used for the auditory device can be used as the arousal device. For example, where a loudspeaker is used as the arousal device, the same loudspeaker can be used as the auditory device.

The auditory output can comprise one or more words, a phrase, a sentence, a nursery rhyme, some or all of a song, or some or all of a poem. The auditory output can comprise a recording such as a recording made by a third person, for example a parent of the subject or a caregiver. In a further embodiment, the recording can be of a favourite actor or fictional character. In another embodiment, the auditory output can comprise a sound or combination of sounds, including a recorded natural sound, for example, a dog bark or a train whistle, or a computer generated sound.

In the case where the control device uses sound recordings, the control device can be provided with a storage device for recording a plurality of auditory outputs, such as a voice/sound recorder, for example a digital voice/sound recorder. The control device can also be provided with a microphone to allow recording of sound. The microphone can be provided separately and be connectable to the control device when required. In another embodiment, the microphone can be incorporated within the control device.

In one embodiment, the storage device can store up to eight different sounds, such as recorded codewords or keywords. The storage device can comprise a non-volatile memory device. In this embodiment, the storage device can operate to play the auditory output only once or a restricted number of times.

In a further embodiment, the control device can comprise a device for recording, storing and/or producing one or more arousal or awakening sounds. The device for recording and storing the one or more arousal or awakening sounds can be a voice/sound recorder, such as a digital voice/sound recorder. The recorder used for storing the arousal or awakening sounds can also be used to store the plurality of auditory outputs. In another embodiment, the control device can be provided with two or more vice/sound recorders, with at least one recorder used for storing a plurality of auditory outputs and at least one being used to store one or more arousal or awakening sounds.

In another embodiment, the one or more arousal or awakening sounds can be electronically synthesized by a sound synthesizer means within the control device.

In yet another embodiment, the audiovisual device can comprise a screen and a loudspeaker that work in combination to deliver an audiovisual output to the subject. The audiovisual output can comprise any combination of the visual and auditory inputs defined herein.

In a still further embodiment, the visual device can comprise a series of coloured lights or light emitting diodes that output different combinations of coloured light and/or lit or non-lit alphanumeric symbols, which may form words, number or word/number/symbol combinations. Still further, different colours and/or symbols can be displayed together with the delivery of different sounds.

By providing devices that allow different combinations of outputs, the subject can be provided with a range of different outputs on actuation of the interactive device. This in part should increase the game-like nature of use of the system and also ensure the subject is not presented with so small a range of outputs that he or she has a reasonably good chance of guessing the output.

The arousal device can comprise an auditory device that outputs an appropriate sound to arouse the subject. In one embodiment, the auditory device can comprise a loudspeaker. The sound can comprise the sound of a bell, a buzzer, an electronically synthesized sound or any other sound suitable for arousing the subject. In a further embodiment, the arousal device can comprise an audiovisual device and/or vibratory device. A vibratory device could be used for example where the subject is deaf or has only partial hearing.

In yet another embodiment, the interactive device can comprise a button, switch or lever that is actuated by the subject. In another embodiment, the interactive device can comprise a proximity sensor and/or movement sensor that detects the presence and/or movement of the subject, for example the presence and/or movement of a hand of the subject. Still further, the interactive device can comprise a touch pad.

In one embodiment, the output device delivers said output immediately on actuation of the interactive device and hence deactivation or modification of the arousal device. The control device can be adapted to not deliver the output to the subject if the arousal device has not been activated by said first signal from the sensor. The control device can also act to not deliver the output if the interactive device has not been actuated to deactivate or modify the arousal device. In another embodiment, the output device can have an in-built delay following deactivation or modification of the arousal device. The delay can be anywhere between a 1 ms to 10 seconds.

The output device can provide the output for a predetermined period. In one embodiment, the output can be provided for anywhere between about 3 seconds and 30 minutes, more preferably between about 3 seconds and 10 minutes, still more preferably between about 3 seconds and 5 minutes, and yet more preferably for about 5 seconds. The output can be provided three times during the predetermined period. In a further embodiment, the control device can have a switch or other similar device to allow the subject or a third party to stop the continuing output from the output device.

In one embodiment, the control device can be arranged to activate the arousal device or an alternative arousal device if the control device is turned off and/or disconnected from a power source, for example mains power, and there has been no delivery of a first signal from the sensor within a predetermined period prior to the device being turned off or losing power. This serves to ensure that the parent or caregiver is informed if the subject has turned off the system following activation when the subject is going to bed.

In another embodiment, the arousal device (or an alternative arousal device) can activate, for at least a relatively short time, for example a few seconds, on switching on of the control device. This serves to reassure the parent or caregiver that the control device is operating correctly prior to use.

In the case of nocturnal enuresis, the sensor can comprise a fluid sensor, and in particular a sensor for the detection of urine. In one embodiment, the sensor can output the first signal on exposure to at least about 1 ml of fluid. The sensor can be adapted to output the first signal on exposure to less than 1 ml or greater than 1 ml of fluid. The sensor can comprise a housing containing componentry. In one embodiment, the componentry can be powered by an on-board power source, such as one or more batteries. The housing can be formed of an electrically resistive material, such as a suitable polymer, for example an ABS plastic.

The sensor can comprise an electrical circuit that conducts electrical current on application of fluid to a desired location in the circuit. The circuit can be formed, at least in part, in or on an outer surface of the housing so that it can be exposed to fluid coming into contact with the sensor. The circuit can be formed on a printed circuit board, such as a flexible printed circuit board or upon a similar substrate including the encasing means of the circuit. The circuit can be formed from a suitable electrically conductive material, such as a laminate of copper or by deposition of a conductive material upon the substrate. If not biocompatible, the electrically conductive material can be coated with a suitable electrically conductive biocompatible material, with examples being platinum or gold.

The fluid sensor can be positionable in underwear pants worn by the subject during sleep. The housing can be suitably shaped to be worn in the pants between the legs and/or adjacent the genitals of the subject. In another embodiment, the sensor can be positionable within a sanitary pad. In one embodiment, the housing can have dimensions of about 40 mm×20 mm×10 mm. In another embodiment, the sensor can extend from a housing containing a wireless transmitter. The housing for the wireless transmitter can be about 69 mm wide and the sensor can be about 10 mm wide and 0.07 mm thick. In yet another embodiment, the housing of the sensor circuit can have dimensions of about 52 mm×26 mm×15 mm.

In one embodiment, a lead can extend from the housing of the sensor to the control device. If used, the lead can be removably or non-removably connectable to the sensor and/or the control device. The lead can be used to allow at least transmission of said first signal from the sensor to the control device. If present, it can also be used to provide power to the componentry of the sensor, with the power being provided by a power source within the control device or a separate device. Transmission of other signals including signals from the control device to the sensor can also be envisaged.

In a preferred embodiment, the sensor can rely on use of a wireless transmitter device which is part of a wireless link provided between the sensor and the control device. The transmitter device can comprise circuitry and an antenna. The transmitter device can be housed within the housing of the sensor or be provided in a separate housing. In the case of a separate housing, the separate housing could be adapted to be worn at another location, for example the waist of the subject, with a suitable lead extending between the housing of the sensor and the separate housing of the wireless transmitter device. The wireless link can use means such as an amplitude shift keying (ASK) RF transmitter or alternatives means having similar function with digital encoding to minimise the likelihood of interference by other wireless links within the vicinity of the system.

The transmitter device preferably only activates on detection of fluid. This serves to relatively increase the life of the on-board power source, where used.

In a still further embodiment, the housing of the sensor can contain a wireless transceiver and be adapted to also receive signals from the control device.

Where the sleep disorder is bruxism, the sensor can be adapted to detect teeth grinding by the subject and output said first signal on or after said detection. In this embodiment, the sensor can be positionable on the jaw and/or the teeth of the subject and be adapted to detect jaw and/or teeth movement indicative of grinding. In another embodiment, the sensor can be a microphone and be adapted to detect the grinding noises generated by a person grinding their teeth together during sleep. In another embodiment the sensor can comprise an electromyographic (EMG) device to detect facial muscle activity. In this application, the sensor can further have one or more of the features of the sensor described herein for use in the detection of urine.

Where the sleep disorder is sleepwalking, the sensor can be adapted to detect movement of the subject from a sleeping to a standing position and output said first signal on or after said detection. In this case, the sensor can be worn on the body and/or clothing of the subject and comprise an accelerometer or other suitable device. In this application, the sensor can further have one or more of the features of the sensor described herein for use in the detection of urine.

Where the sleep disorder is sleep talking, the sensor can be adapted to detect the sounds of sleep talking and/or comprise an electromyographic (EMG) device to detect facial muscle activity and output said first signal on or after said detection. In this embodiment, the sensor could be worn on the subject or be positioned relatively close to the subject, for example, in or on a pillow, a bed head or bedside table. The sensor could be a microphone or EMG electrodes. In this application, the sensor can further have one or more of the features of the sensor described herein for use in the detection of urine.

Where the sleep disorder is night terrors, the sensor can be adapted to detect head movements and/or sounds or the electroencephalographic (EEG) manifestations of stress generated by the subject and output said first signal on or after said detection. In this embodiment, the sensor could comprise a movement sensor, such as an accelerometer. In this application, the sensor can further have one or more of the features of the sensor described herein for use in the detection of urine.

In a further embodiment, the control device can comprise a wireless receiver device and an antenna and be capable of detecting signals output from the wireless transmitter of the sensor. In another embodiment, the control device can have a wireless transceiver device and antenna and be capable of outputting signals to the sensor.

According to a third aspect, the present application is a system for use by a subject suffering nocturnal enuresis comprising:
  a fluid sensor that outputs at least a first signal on detection of a fluid; and
  a control device comprising:
    an arousal device that activates on or after receipt of said first signal by said control device;
    an interactive device actuable by said subject to deactivate or modify the operation of said arousal device; and
    an output device for delivering an output to said subject, said output being delivered on or after deactivation or modification of the arousal device.

According to a fourth aspect, the present application is a control device for use by a subject suffering nocturnal enuresis comprising:
  an arousal device that activates on or after receipt by said control device of a first signal from a fluid sensor;
  an interactive device actuable by said subject to deactivate or modify the operation of said arousal device; and
  an output device for delivering an output to said subject, said output being delivered on or after deactivation or modification of the arousal device.

In the third and fourth aspects, system and/or device can have, where appropriate, one, some or all of the features as defined herein with reference to the first and second aspects.

According to a fifth aspect, the present application is a method of encouraging, through use of a game, arousal of a subject suffering a sleep disorder, the method comprising:
  informing the subject that an award will be given for successful completion of the game;
  informing the subject what they need to do successfully complete the game;
  using a sensor that detects at least one attribute of the sleep disorder of the subject and outputs at least a first signal on or after detection of the said attribute;
  arousing the subject using an arousal device on receipt of said first signal by said control device;
  determining if the subject has been aroused by sensing actuation of an interactive device by the subject;
  outputting an output to the subject;
  subsequently determining from the subject the nature of the output; and
  rewarding the subject if the subject correctly identifies the output.

In this aspect, the incorporation of a game, namely the successful identification of the output, is anticipated by the present inventors to increase the likelihood of ensuring the subject, particularly a child, awaking sufficiently to allow treatment of the sleep disorder. Where the child suffers from nocturnal enuresis, the degree of arousal required to identify and remember the output is also likely to be sufficient to result in the subject going to the toilet. Over time, through continued use of the game, it is anticipated that the subject will no longer require arousal by the arousal device to realise they have a full bladder and need to go to the toilet.

In this aspect, the method can be performed using the system as defined herein with respect to the earlier aspects. The steps of informing and rewarding the subject can be performed by a parent or caregiver. Still further, the parent or caregiver can use the control device as defined herein to store a code word or other suitable output on the device.

BRIEF DESCRIPTION OF THE DRAWINGS

By way of example only, embodiments are now described with reference to the accompanying drawings, in which.

EMBODIMENTS

Figure 1:
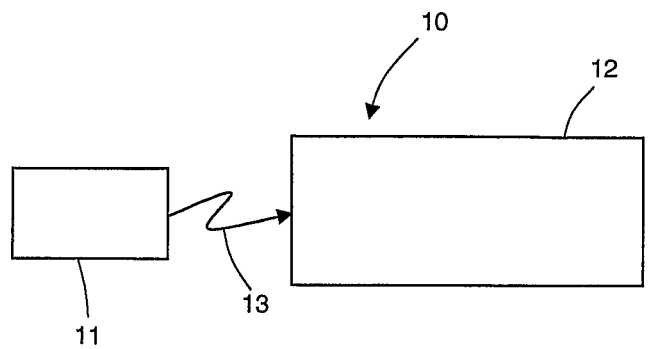
FIG. 1 is a schematic representation of one embodiment of the system as described herein.

The present application is directed in part to a system that can be used by persons suffering certain kinds of sleep disorders and where it is desired to arouse the person from sleep to a desired arousal level. In the attached drawings and the following description, a system for use by children suffering enuresis, particularly nocturnal enuresis, is described. It will be appreciated that the depicted system can be used for adolescents and adults and, with appropriate modification, particularly to the sensor, for use in the treatment of other disorders including bruxism, sleepwalking, sleep talking, and/or night terrors.

One embodiment of the system for use in the treatment of a subject, particularly a child, suffering from nocturnal enuresis is depicted generally as 10 in the drawings.

The system 10 comprises at least one urine sensor 11 that outputs at least a first signal 13, on or after detection of urine or other fluid, via a wireless link to a control device 12.

Figure 2:
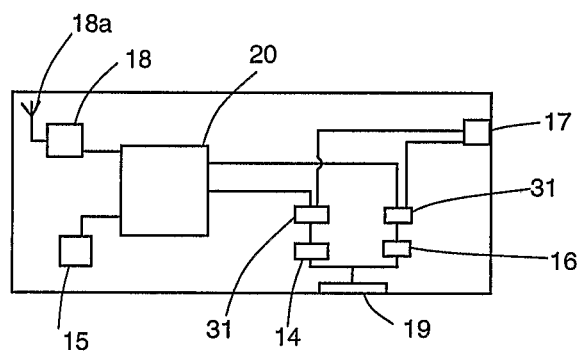
FIG. 2 is a schematic representation of one embodiment of the control device as defined herein.

As depicted schematically in FIG. 2, the control device 12 comprises a number of components controlled by a central processor 20. The control device includes a wireless receiver 18 and an antenna 18a that act as part of the wireless link and which receive at least the first signal 13 from the sensor 11. In one embodiment, the receiver 18 can comprise a RWS 434 RF Receiver as supplied by Reynolds Electronics (Canon City, Colo., United States of America). This receiver operates at a frequency between 433.90 to 433.94 MHz. As well as receiving, it will be appreciated that the receiver device 18 and antenna 18a could be modified to act as a transceiver and so be capable, if desired, of outputting one or more appropriate signals to the sensor 11. The control device 12 can be mains powered and/or rely on an on-board power source, for example one or more batteries.

Figure 4:
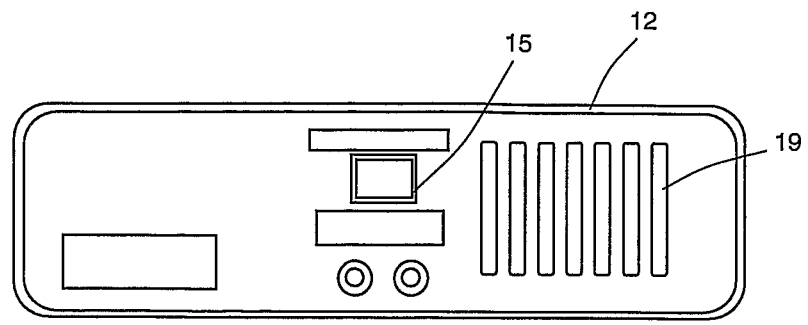
FIG. 4 is a depiction of the front panel of a prototype control device as defined herein.

While described in more detail below, the control device 12 further comprises:

an arousal device 14 that activates on or after receipt of the first signal 13 by the control device 12;

an interactive device 15, in FIG. 4 an illuminated depressible button, that is actuable by the child and which on actuation deactivates or otherwise modifies the operation of the arousal device 14; and an output device 16 that provides an output to the child.

The output of the output device 16 is preferably only provided on or after deactivation or modification of the arousal device 14.

The system 10 can be used to perform a method of encouraging, through use of a game, a subject, such as a child, to arouse from sleep for the purpose of treating a sleep disorder like nocturnal enuresis. In addition to using the system 10, a parent or caregiver will need to encourage the child to participate in the treatment. This can be done by firstly informing the child that a reward will be given for successful completion of the game and explaining what needs to be done to successfully complete the game. Rather than necessarily awarding a dry night, the present system rewards the child if they achieve a level of cognitive arousal sufficient to note and remember the output of the output device 16.

The sensor 11 can then be appropriately positioned to detect urine and the control device 12 turned on. After a period of time in which it is assumed the child is asleep, the sensor 11 provides the first signal 13 if it detects urine. The control device inside 12 then activates the arousal device 14 to awaken the child. The method determines if the child has been aroused by awaiting actuation of the interactive device 15. On or after actuation, the output device 16 delivers the output to the child. In the morning or at some other time, the parent or caregiver can question the child as to the nature of the output from the output device 16 that was delivered. Successful identification of the output should then result in the provision to the child of the promised reward.

The incorporation of a game, namely the successful identification of the output, is anticipated by the present inventors to increase the likelihood of ensuring the child awakes sufficiently to allow treatment of the nocturnal enuresis. The degree of arousal required to identify and remember the output is also likely to be sufficient to result in the child realising they have a full bladder so going to the toilet to void. Over time, through continued use of the game, it is anticipated that the child will no longer require arousal by the arousal device 14 to realise they have a full bladder and need to go to the toilet.

The output of the output device 16 can change each time that the interactive device 15 is appropriately actuated by the child following operation of the arousal device 14. In another embodiment, the output can change from use to use or night to night for a period before recycling. If the outputs are recycled, they can recycle in the same order or a different order to a previous cycle.

In the embodiment depicted in the drawings, the output of the output device 16 is provided to an auditory device in the form of a loudspeaker 19. This loudspeaker 19 can also be activated by the arousal device 14 to awaken the child.

The volume of the output from the loudspeaker 19 can be pre-set or adjustable. Preferably, adjustment of the volume requires entry of a code or the like to prevent the child undesirably lowering the volume. The volume can be different when the loudspeaker 19 is used to arouse the child as to when it is used to deliver an auditory output. As an example only, the volume of the auditory output from the loudspeaker 19 when used as the output device 16 can be about 90 dB if heard at a distance of 30 cm (or 85 dB(A) if heard at a distance of 1 m). Use of relatively louder or softer volumes can be envisaged.

The auditory output from the loudspeaker 19 can comprise one or more words, a phrase, a sentence, a nursery rhyme, some or all of a song, or some or all of a poem. The auditory output can comprise a recording such as a recording made by a third person, for example a parent of the subject or a caregiver. It can instead comprise a recording from a favourite actor or fictional character known to the child. In another embodiment, the auditory output can comprise a sound or combination of sounds, including a recorded natural sound, for example, a dog bark or a train whistle, or a computer generated or electronically synthesized sound.

In the case where the control device 12 uses sound recordings, both the arousal device 14 and the output device 16 can rely on a data storage device for storing a plurality of sound outputs. In the depicted device, the data storage device in each instance can comprise a digital voice recorder 31 that receives signals from a microphone 17. The digital voice recorders can be provided as a kitset by Jaycar™, part number KC5454. In the depicted embodiment, the microphone 17 is built-in to the control device 12. It will be appreciated that in another arrangement, the microphone could be provided separately and be connectable to the control device 12 when required. While separate digital voice recorders 31 are depicted, the control device 12 could be provided with a single voice recorder that is capable of storing both the arousal or awakening sounds and the auditory output generated following actuation of the interactive device 15.

Figure 5:
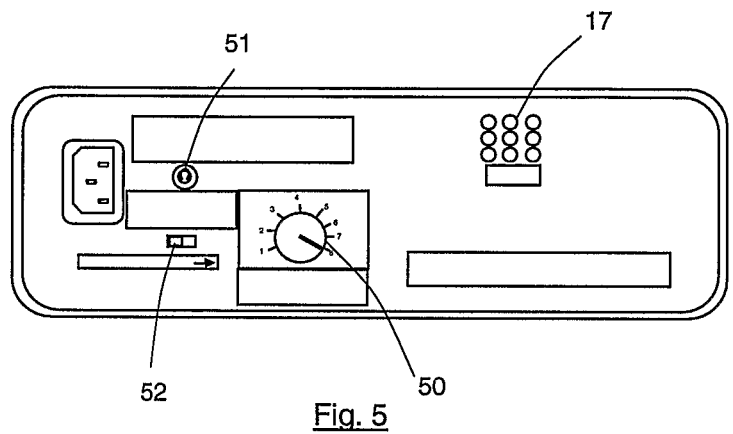
FIG. 5 is a depiction of the rear panel of a prototype control device as defined herein.

Each digital voice recorder 31 of the depicted embodiment comprises a non-volatile memory device and can store up to eight different sound recordings; such as recorded codewords or keywords, for use as the auditory output or up to eight sound recordings of the awakening sound. The parent or caregiver may be asked to deliver the codeword on more than one occasion, for example three times. Each recording can be preset to be about 5 seconds long. The control device 12 can have a playback feature that allows the parent or caregiver to check the recording of they keyword. In the depicted arrangement, the output device 16 is set-up to play one stored recording repetitively on actuation of the interactive device 15 following operation of the arousal device 14. Control of the digital voice recorders can be provided through use of the knob 50 and switches 51,52 as provided on the rear panel of the device 12 as depicted in FIG. 5. In this embodiment, knob 50 controls which of the 8 keywords is being recorded and/or output by the device 12. The 3-position, centre off switch 51 actuates the digital voice recorders 31 to allow both recording and playback of the keyword and switch 52 disables the ability to record, playback or delete a recording. If desired, switch 52 can be locked, for example, through use of a key.

The control device 12 can also rely on an audio amplifier to provide appropriate amplification of the sounds recorded by the digital voice recorders 31 if required.

It will be appreciated that in other arrangements, the output device 16 could comprise a visual display device, an audiovisual device, or a device that is touchable by the child and which has a distinctive feel that can be described by the child. This latter embodiment may have application for children that are blind or have impaired eyesight and/or hearing.

If a visual display device or audiovisual device is used, it can comprise a display screen, for example a television screen, a projection screen, a liquid crystal display (LCD) screen or a plasma screen. The screen can display a number, a word, a symbol, a picture, a photo, a colour, and/or a combination of any of these.

If used, the audiovisual device can comprise a screen and loudspeaker that work in combination to deliver an audiovisual output to the child. The audiovisual output can comprise any combination of the visual and auditory inputs as defined herein.

In yet another arrangement, the visual device could comprise a series of coloured lights or light emitting diodes that output different combinations of coloured light and/or lit or non-lit alphanumeric symbols, which may form words, number or word/number/symbol combinations. Still further, different colours and/or symbols can be displayed together with the delivery of different sounds.

By providing devices that allow different combinations of outputs, the child can be provided with a range of different outputs on actuation of the interactive device 15. This in part should increase the game-like nature of use of the system 10 and also ensure the child is not presented with so small a range of outputs that he or she has a reasonably good chance over time of guessing the output.

As mentioned, the arousal device 14 can comprise an auditory device that outputs an appropriate sound to arouse the subject, and can use the loudspeaker 19. The sound delivered by the arousal device 14 can comprise the sound of a bell, a buzzer, an electronically synthesized sound or any other sound suitable for arousing the child. The volume is preferably relatively loud to ensure the child is awakened quite quickly following operation.

It will be appreciated that the arousal device 14 could comprise an audiovisual device and/or vibratory device. A vibratory device could be used for example where the child is deaf or has only partial hearing.

A number of different types of interactive device 15 can be used as part of the present system. In the embodiment depicted in FIG. 4, the interactive device 15 comprises an illuminated button that should be depressed and then released by the child when they are awoken by the arousal device 14. It will be appreciated that the interactive device 15 can comprise any type of suitable switch or lever or even a touch pad. In another arrangement, the interactive device 15 can comprise a proximity sensor and/or movement sensor that detects the presence and/or movement of the child, for example the presence and/or movement of a hand of the child.

In the depicted arrangement, the output device 16 delivers the output immediately on actuation of the interactive device 15 and hence deactivation of the arousal device 14. The control device 12 can be adapted to not deliver the output to the child if the arousal device 14 has not been activated by arrival of the first signal 13 from the sensor 11. The control device 10 can also act to not deliver the output if the interactive device 15 has not been actuated to deactivate the arousal device 14. In another embodiment, the output device 16 can have an in-built delay following deactivation of the arousal device 14. The delay can be anywhere between a 1 ms to 10 seconds.

The output device 16 can provide the output for a predetermined period. In one embodiment, the output can be provided for anywhere between about 3 seconds and 30 minutes, more preferably between 3 seconds and 10 minutes, still more preferably between about 3 seconds and 5 minutes, and yet more preferably for about 5 seconds. The output can be provided three times in the predetermined period. In a further embodiment, the control device 10 can have a switch or other similar device to allow the subject or a third party to stop the continuing output from the output device 16.

On activation of the arousal device 14, the control device 12 can issue an output indicative that the sensor is wet. This output may comprise illumination or flashing of an LED or display of a message.

In one embodiment, the control device 10 can be arranged to activate the arousal device 14 (or an alternative arousal device if provided) if the control device 10 is turned off and/or disconnected from a power source, for example mains power, and there has been no delivery of a first signal 13 from the sensor 11 within a predetermined period prior to the device 12 being turned off or losing power. This serves to ensure that the parent or caregiver is informed if the child has turned off the system 10 following activation when the child is going to bed.

The arousal device 14 (or alternative arousal device if provided) can also activate, for at least a relatively short time, for example a few seconds, on switching on of the control device 12. This serves to reassure the parent or caregiver that the arousal device 14 is operating correctly prior to use. It also indicates that power to the control device 12 is present and that the output device is not yet switched on.

In the case of nocturnal enuresis, the sensor 11 can comprise a fluid sensor, and in particular a sensor for the detection of urine. The sensor 11 can output the first signal 13 on exposure to at least about 1 ml of fluid. The sensor 11 can be adapted to output the first signal 13 on exposure to less than 1 ml or greater than 1 ml of fluid. If desired, the system 10 can allow testing of the operation of the system, including the sensor 11.

The sensor 11 can comprise a housing 21 containing componentry. The componentry can be powered by an on-board power source 32, such as one or more batteries (e.g. a 2032 $LiMnO_2$ cell). The housing 21 can be formed of an electrically resistive material, such as a suitable polymer, for example an ABS plastic.

The sensor 11 can comprise an electrical circuit 33 that is part of sensing circuit 34 that conducts electrical current on application of fluid to a desired location in the circuit. The circuit 33 can be formed, at least in part, in or on an outer surface of the housing 21 so that it can be exposed to fluid coming into contact with the sensor 11. The circuit 33 can be formed on a printed circuit board, including a flexible printed circuit board. The circuit 33 can be formed on a printed circuit board, such as a flexible printed circuit board or upon a substrate that is part of the housing of the sensor. The circuit can be formed from a suitable electrically conducting material, such as a laminate of copper or by deposition of a conductive material upon the substrate. If not biocompatible, the electrically conductive material can be coated with a suitable electrically conductive biocompatible material, with examples being platinum or gold.

The fluid sensor 11 can be positionable in underwear pants worn by the child during sleep. The housing 21 can be suitably shaped to be worn in the pants between the legs and/or adjacent the genitals of the child. The sensor can be positionable within a sanitary pad. While other dimensions are envisaged, the housing 21 can have dimensions of, for example, about 40 mm×20 mm×10 mm or 52 mm×26 mm×15 mm.

A lead can be provided that extends from the housing 21 of the sensor 11 to the control device 12. If used, the lead can be removably or non-removably connectable to the sensor 11 and/or the control device 12. The lead can be used to allow at least transmission of said first signal 13 from the sensor 11 to the control device 12. If present, it can also be used to provide power to the componentry of the sensor 11, with the power being provided by a power source within the control device 12 or a separate device. Transmission of other signals including signals from the control device 12 to the sensor 11 can also be envisaged.

Figure 3:
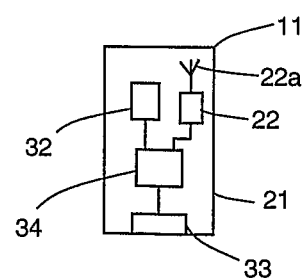
FIG. 3 is a schematic representation of one embodiment of the sensor as defined herein.
Figure 6A:
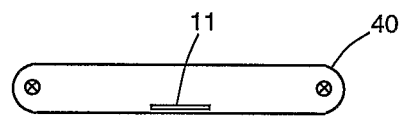
FIGS. 6a and 6b are side elevation and plan views of an embodiment of the sensor and wireless transmitter as defined herein.
Figure 6B:
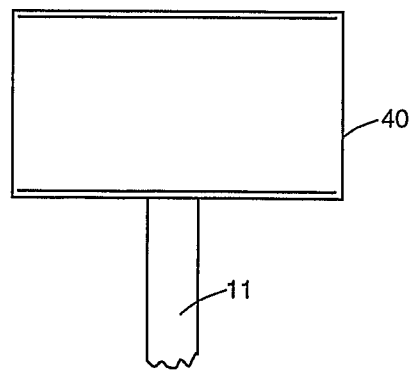

As depicted, it is preferred that the sensor 11 rely on use of a wireless transmitter device 22 and antenna 22a which is part of a wireless link provided between the sensor 11 and the control device 12. The transmitter device 22 can be housed within the housing 21 of the sensor 11, as depicted schematically in FIG. 3, or be provided in a separate housing 40 as depicted in the embodiment depicted in FIGS. 6a and 6b. In one embodiment, the sensor 11 can extend from the housing 40. The housing for the wireless transmitter can be about 69 mm wide and the sensor can be about 10 mm wide and 0.07 mm thick. In another embodiment, the separate housing 40 can be adapted to be worn at another location, for example the waist of the subject, with a suitable lead extending between the housing of the sensor 11 and the separate housing of the wireless transmitter device.

The wireless link between the sensor 11 and the control device 12 can use an RWS-434 RF Transmitter (Reynolds Electronics, Canon City, Colo., United States of America) and an amplitude shift keying (ASK) RF transmitter with an encoder (e.g. a Reynolds Electronics CIP-8 series 8-bit encoder/decoder IC) to minimise the likelihood of interference from other wireless links within the vicinity of the system 10. Instead of amplitude shift keying (ASK), alternatives means having similar function with digital encoding to minimise the likelihood of interference by other wireless links within the vicinity of the system can be used.

The transmitter device 22 preferably only activates on detection of fluid. This serves to relatively increase the life of the on-board power source 32, where used.

It will be appreciated that the housing of the sensor 11 could contain a wireless transceiver and be adapted to also receive signals from the control device 12.

As discussed, the system 10 can be used to treat sufferers of types of sleep disorders other than enuresis.

Where the sleep disorder is bruxism, the sensor 11 can be modified from that depicted and be capable of detecting teeth grinding by the subject and then output a first signal on or after such detection. When used in this application, the sensor 11 can be positionable on the jaw and/or the teeth of the subject and be adapted to detect jaw and/or teeth movement indicative of grinding. In another arrangement, the sensor 11 can be a microphone and be adapted to detect the grinding noises generated by a person grinding their teeth together during sleep. In this application, the sensor 11 can further have one or more of the features of the sensor described herein for use in the detection of urine.

Where the sleep disorder is sleepwalking, the sensor 11 can be modified from that depicted and used to detect movement of the subject from a sleeping to a standing position and output a first signal on or after said detection. In this case, the sensor 11 can be worn on the body and/or clothing of the subject and comprise an accelerometer or other suitable device. In this application, the sensor 11 can further have one or more of the features of the sensor described herein for use in the detection of urine.

Where the sleep disorder is sleep talking, the sensor 11 can be modified from that depicted and used to detect the sounds of sleep talking and output a first signal on or after said detection. In this embodiment, the sensor 11 could be worn on the subject or be positioned relatively close to the subject, for example, in or on a pillow, a bed head or bedside table. The sensor could be a microphone. In this application, the sensor 11 can further have one or more of the features of the sensor described herein for use in the detection of urine.

Where the sleep disorder is night terrors, the sensor 11 can be modified from that depicted and used to detect head movements and/or sounds generated by the subject and output a first signal on or after said detection. In this embodiment, the sensor 11 could comprise a movement sensor, such as an accelerometer. In this application, the sensor 11 can further have one or more of the features of the sensor described herein for use in the detection of urine.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

The invention claimed is:

1. A method of encouraging, through use of a game, arousal of a subject suffering a sleep disorder, the method comprising:
    informing the subject that an award will be given for successful completion of the game;
    informing the subject what the subject needs to do to successfully complete the game;
    detecting through use of a sensor at least one attribute of the sleep disorder of the subject, wherein the sensor outputs at least a first signal on or after detection of the said attribute;
    arousing the subject using an arousal device on receipt of said first signal by a control device;
    determining if the subject has been aroused by sensing actuation of an interactive device by the subject;
    outputting an output to the subject based on said sensing of said actuation;
    subsequently determining from the subject the nature of the output; and
    rewarding the subject if the subject correctly identifies the output.

2. The method of claim 1 wherein each output to the subject on each operation is different to that delivered the immediately previous time.

3. The method of claim 1 wherein the outputs are recycled.

4. The method of claim 3 wherein when the outputs are recycled in a different order to the order of the outputs in the immediately previous cycle.

5. The method of claim 1 wherein the output is delivered to the subject by an output device.

6. The method of claim 5 wherein the output device is a visual display device, an auditory device, and/or an audiovisual device.

7. The method of claim 6 wherein the auditory device comprises a loudspeaker that outputs an auditory output.

8. The method of claim 7 wherein the loudspeaker is also used as the arousal device.

9. The method of claim 7 wherein the auditory output comprises a recording of one or more words, a phrase, a sentence, a nursery rhyme, some or all of a song, or some or all of a poem.

10. The method of claim 1 wherein the sensor has a wireless transmitter or wireless transceiver which is part of a wireless link provided between the sensor and the control device.

11. The method of claim 5 wherein the output device delivers said output immediately on actuation of the interactive device.

12. The method of claim 1 or claim 9 wherein the control device comprises a storage device for storing a plurality of sound outputs and a microphone.

13. The method of claim 1 wherein the control device comprises a device for recording or producing one or more arousal or awakening sounds.

14. The method of claim 1 wherein the interactive device comprises a button, a switch, a lever, a proximity sensor, a movement sensor, and/or a touch pad.

15. The method of claim 1 wherein the sensor comprise a sensor for the detection of urine.

16. The method of claim 10 wherein the control device comprises a wireless receiver or wireless transceiver that detects signals output from the sensor.

17. The method of claim 1 wherein the sensor detects teeth grinding by the subject, and/or movement of the subject from a sleeping to a standing position, and/or the sounds of sleep talking by the subject, and/or head movements by the subject.

* * * * *